United States Patent
Vladimirsky

(10) Patent No.: US 7,465,294 B1
(45) Date of Patent: Dec. 16, 2008

(54) RETRACTABLE HYPODERMIC NEEDLE

(76) Inventor: Roman Vladimirsky, 2700 N. Cahuenga Blvd., #3109, Los Angeles, CA (US) 90068

( * ) Notice: Subject to any disclaimer, the term of this patent is extended or adjusted under 35 U.S.C. 154(b) by 690 days.

(21) Appl. No.: 11/014,023

(22) Filed: Dec. 15, 2004

Related U.S. Application Data

(60) Provisional application No. 60/572,445, filed on May 19, 2004.

(51) Int. Cl.
*A61M 5/32* (2006.01)
(52) U.S. Cl. ...................... 604/192; 604/198
(58) Field of Classification Search ............ 604/110, 604/272, 192, 195, 198
See application file for complete search history.

(56) References Cited

U.S. PATENT DOCUMENTS

| | | | | |
|---|---|---|---|---|
| 4,781,692 A * | 11/1988 | Jagger et al. | ........... | 604/164.08 |
| 5,053,010 A * | 10/1991 | McGary et al. | ........... | 604/110 |
| 5,084,018 A * | 1/1992 | Tsao | ........... | 604/110 |
| 5,267,976 A * | 12/1993 | Guerineau et al. | ........... | 604/198 |
| 5,762,634 A * | 6/1998 | Davis | ........... | 604/195 |
| 6,364,869 B1 * | 4/2002 | Bonaldo | ........... | 604/537 |
| 2002/0045843 A1 * | 4/2002 | Barker et al. | ........... | 600/585 |
| 2002/0103499 A1 * | 8/2002 | Perez et al. | ........... | 606/182 |
| 2003/0236501 A1 * | 12/2003 | Donnan et al. | ........... | 604/192 |
| 2004/0138619 A1 * | 7/2004 | Kiehne | ........... | 604/164.01 |

* cited by examiner

*Primary Examiner*—Nicholas D Lucchesi
*Assistant Examiner*—Aarti Bhatia
(74) *Attorney, Agent, or Firm*—Allan M. Shapiro

(57) ABSTRACT

A needle assembly includes a sheath into which a hypodermic needle is withdrawn in a protected position. Installation of the needle assembly onto a Luer lock causes the needle to be thrust forward out of the sheath. A spring urges the needle to the withdrawn position. An elastomeric ball in the needle assembly provides sealing.

20 Claims, 3 Drawing Sheets

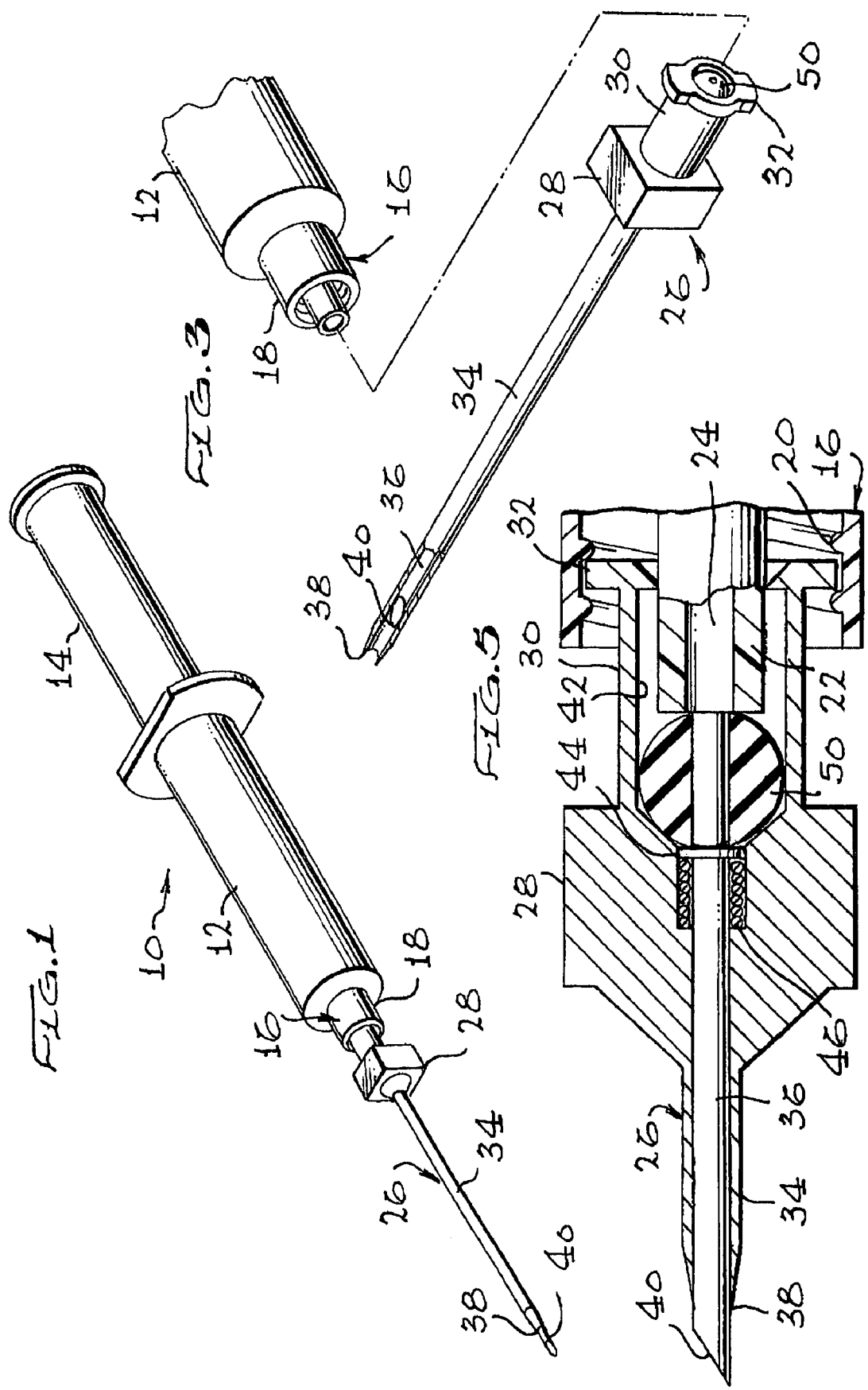

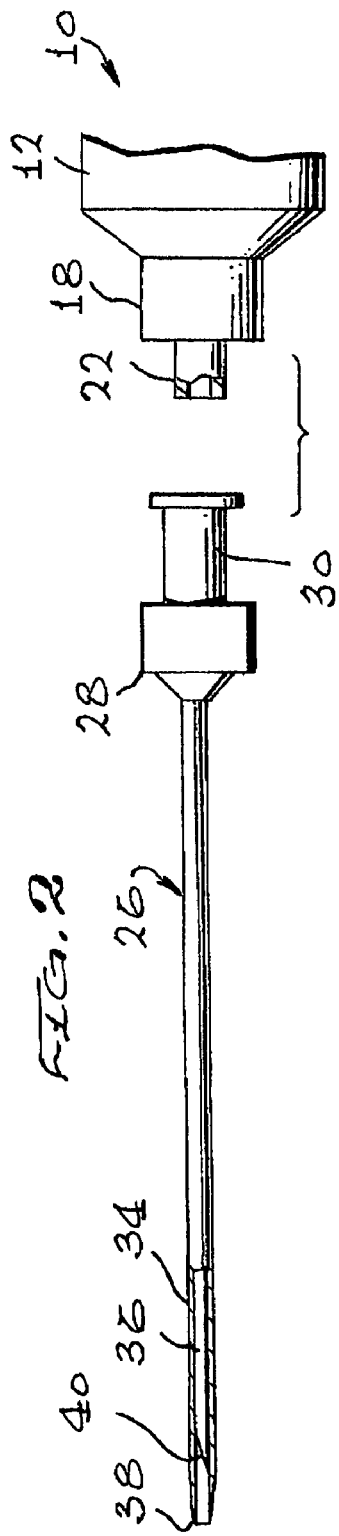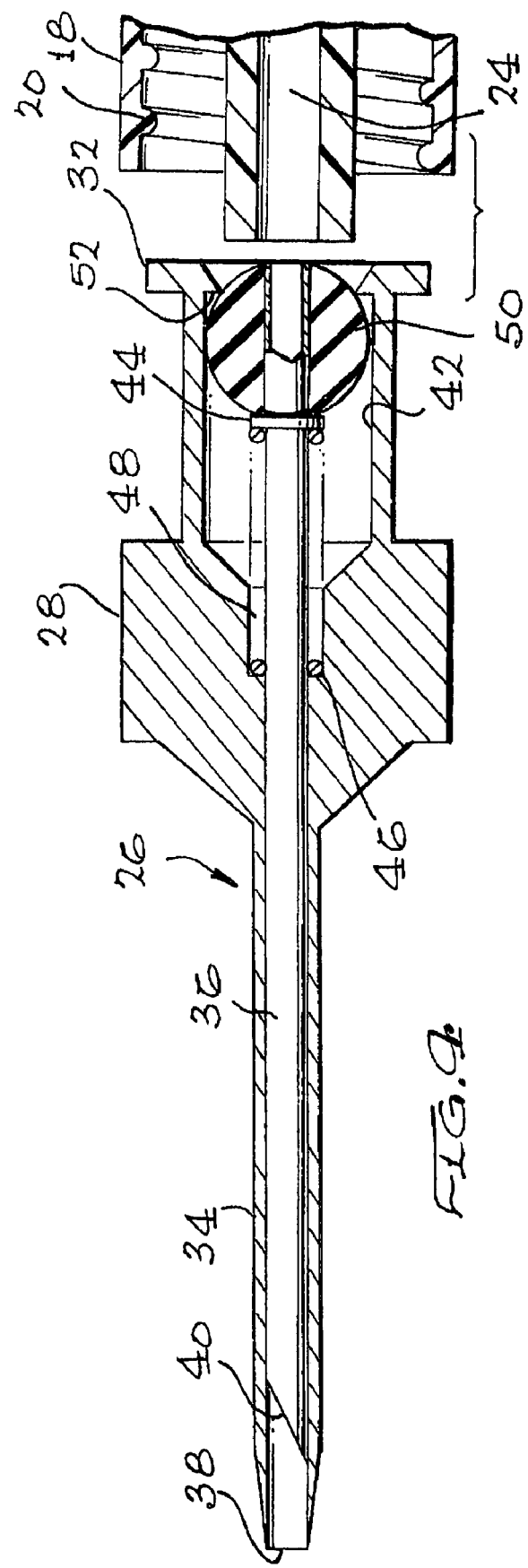

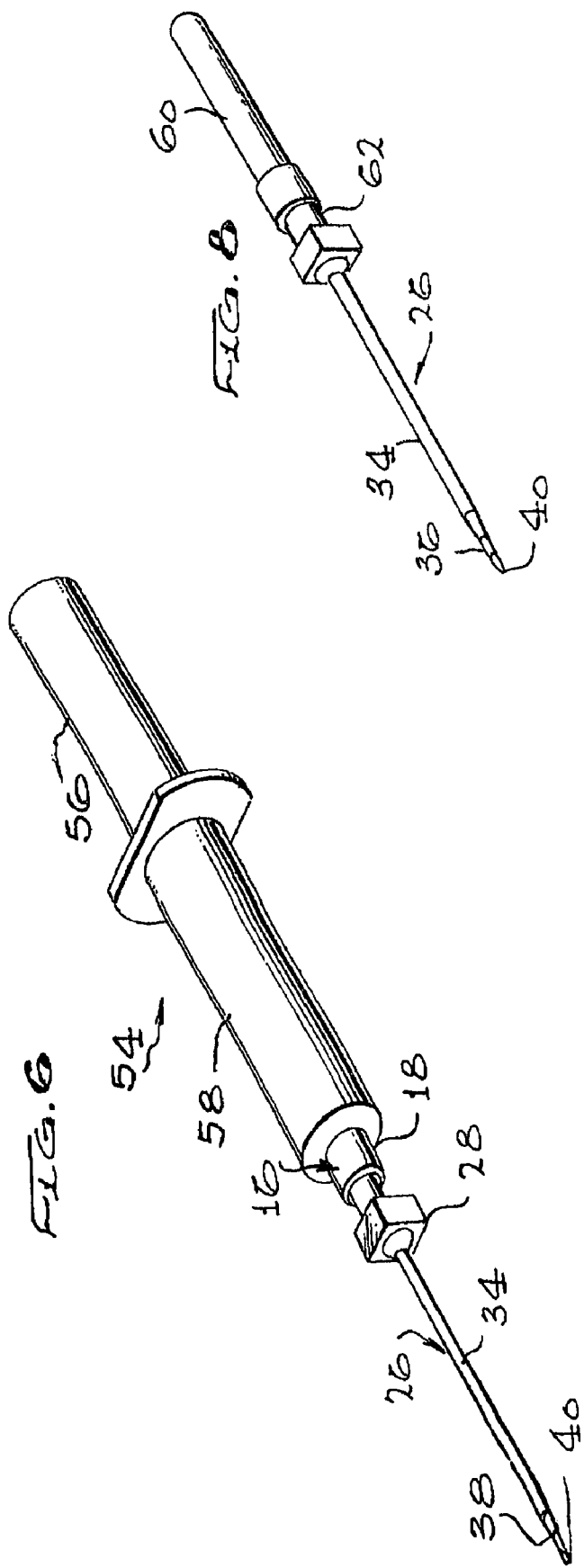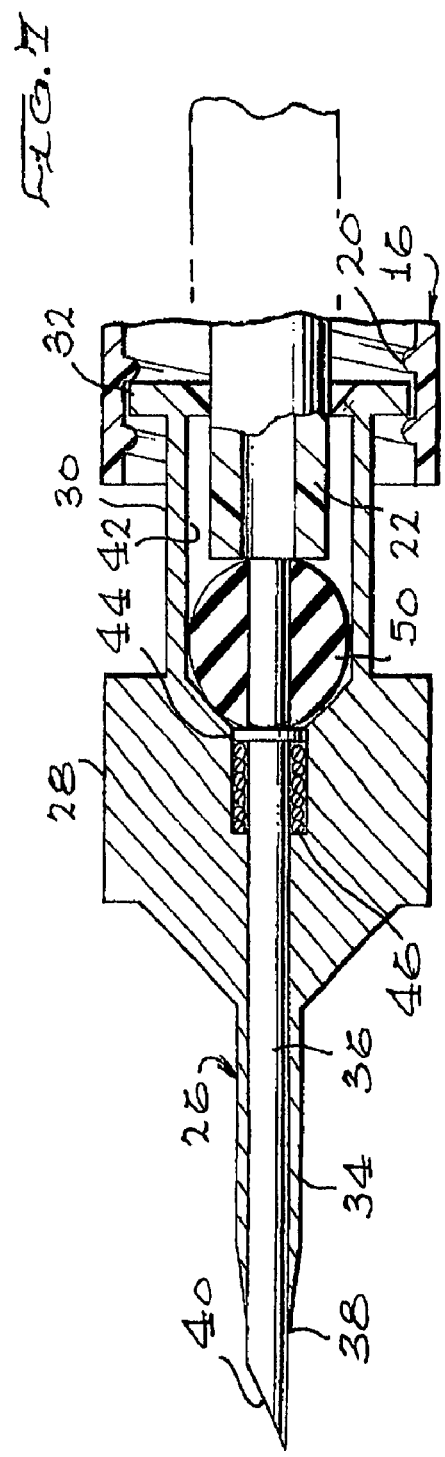

US 7,465,294 B1

RETRACTABLE HYPODERMIC NEEDLE

CROSS-REFERENCE

This application relies for priority on my application Ser. No. 60/572,445, filed May 19, 2004.

FIELD OF THE INVENTION

This invention is directed to hypodermic needle system wherein the needle is retracted into its sheath when the needle assembly is removed from a syringe, to protect personnel against inadvertent needle sticks.

BACKGROUND OF THE INVENTION

Hypodermic needles are used in medicine both to inject liquid materials into the body and to withdraw samples from the body. The usual withdrawal is the withdrawal of venous blood. Many infectious diseases are carried in the blood. It has become important in the medical arts to protect the practitioners from contact with possibly-infectious blood. Skin surface contact with blood and other body fluids is not particularly harmful, especially when the skin is healthy. The larger danger for medical practitioners is the possibility of being inadvertently stuck by a needle which carries on it elements of another person's blood. Quite a number of different apparatuses and protocols have been created to minimize risk of inadvertent sticking by a used hypodermic needle. These dangers require the need for advances in the protection from hypodermic needles, and particularly an operative system whereby the hypodermic needle is automatically withdrawn into the retracted position when the needle assembly is unmounted.

SUMMARY OF THE INVENTION

In order to aid in the understanding of this invention, it can be stated in essentially summary form that it is directed to a retractable hypodermic needle which is mounted in an assembly including a needle sheath. The assembly body, which carries the needle sheath, is mountable on a Luer lock syringe. When mounted, the nozzle of the Luer lock extends the needle from its sheath, and when demounted, the needle is retracted into its sheath.

It is thus a purpose and advantage of this invention to provide a hypodermic needle which is in the retracted position within a sheath when it is not mounted on a syringe or similar structure.

It is another purpose and advantage of this invention to provide a needle assembly which mounts on a Luer lock. The needle assembly includes a needle which is retracted into a needle sheath when not mounted. The needle is extended from the needle assembly when the needle assembly is mounted on a Luer lock structure.

It is another purpose and advantage of this invention to provide a retractable hypodermic needle which is useful both for the injection of medication and for the withdrawal of body fluids, with the needle retracting into its sheath when the needle assembly is removed from its mounting.

It is another purpose and advantage of this invention to provide a retractable hypodermic needle assembly which is inexpensive to build, reliable to use and maintains the needle when withdrawn into its needle sheath whenever the needle assembly is not mounted.

The features of this invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is an isometric view of a syringe with the retractable hypodermic needle assembly of this invention mounted thereon.

FIG. 2 is an enlarged side elevational view thereof, in disassembled form with parts broken away and parts taken in section.

FIG. 3 is an isometric disassembled view, with parts broken away.

FIG. 4 is an enlarged side elevational view, similar to FIG. 2, taken generally along a center line section, with parts broken away.

FIG. 5 is a view similar to FIG. 4, showing the needle assembly attached to the Luer lock nozzle of a hypodermic syringe or the like.

FIG. 6 is a view similar to FIG. 1, showing the needle assembly attached to a needle holder and a blood collection tube in a phlebotomy set.

FIG. 7 is an enlarged view of the phlebotomy set taken substantially along a center line section, with parts broken away.

FIG. 8 is an isometric view of the needle assembly of this invention attached to a Luer lock on the end of an intravenous catheter tube, usually used for introducing intravenous fluid.

DESCRIPTION OF THE PREFERRED EMBODIMENTS

Syringe 10 is shown in FIG. 1. The syringe 10 is of conventional configuration. It has a barrel 12 in which is slidably-disposed plunger 14. The plunger can slide within the barrel to receive or dispense fluid therefrom. The barrel carries Luer lock 16 thereon. The Luer lock comprises a collar 18 which has interrupted interior threads 20 and nozzle 22 which extends past the collar 18. Nozzle 22 is tapered and has an interior passage 24 which extends into the interior of the barrel. Thus, depression and retraction of plunger 14 moves fluid through passage 24 into or out of the syringe barrel. This is conventional construction.

The retractable hypodermic needle assembly of this invention is generally indicated at 26 in FIGS. 1, 2, 3, 4, 5, 6, 7 and 8. It comprises a body 28. In the right hand of the body is formed tube 30 which carries fingers 32. The fingers are configured to enter into the collar 18 and engage on the interrupted threads 20 therein. It is these fingers which retain the needle assembly 26 on the syringe 10. This is common Luer lock construction. The other end of the body 28 carries needle sheath 34. The needle sheath is a tube which slidably carries the needle 36 therein. The needle sheath terminates in a blunt end 38. The needle has a diagonally-cut sharp end 40. The sharp end is retracted into the needle sheath 34 in FIG. 4 and is extended in FIG. 5.

The needle 36 extends backward through the body 28. Within the seal cavity 42, within tube 30, spring stop collar 44 is part of the needle. Compression spring 46 surrounds the needle, engages against the spring stop 44 and lies within the spring pocket 48 in body 28. The spring urges the needle to the right, retracted position shown in FIG. 4. To the right of spring stop collar 44, elastic ball 50 engages around the needle tube. In the retracted, right-most position of the needle seen in FIG. 4, ball 50 is engaged against circular lip 52 which surrounds the right end of seal cavity 42. The ball engages against the interior of the seal cavity, engages against the outside of the needle tube and engages against the spring stop collar 44, as shown in FIG. 4. The ball serves as a retracted position stop for the needle, when it is withdrawn into the sheath by compression spring 46 as shown in FIG. 4. This is a safe position where the sharp end 40 of the needle is withdrawn into the sheath 34. The needle will stay in the retracted position until it is forced out into active position.

When it is desired to use the syringe to inject liquid, the needle assembly 26 is assembled onto the Luer lock of syringe 10. As seen in FIG. 5, the nozzle 22 of the syringe engages against the ball 50 and presses the ball leftward in the seal cavity 42 until it engages against the left end of the cavity. At this point, the stop collar 44 is at the entrance of the spring pocket 48. In this position the sharp end 40 of the needle 36 extends past the blunt end 38 of the needle sheath 34. The hypodermic syringe and the needle assembly are now ready for insertion and injection. Immediately after injection, the needle is withdrawn from the patient. Thereupon, the needle assembly is removed from the syringe. Upon removal, the nozzle 22 no longer holds the needle to the exposed, left position, but the compression spring 46 moves the needle 36 and ball 50 to the right to the retracted position shown in FIG. 4. Now the needle is thrown away. As soon as the needle is retracted into the sheath, the needle is safe. The various dimensions can be established in accordance with the amount of needle exposure which is required. Only the needle touches the patient, and as soon as the tip of the needle is retracted into its sheath, the needle is safe.

FIGS. 6 and 7 illustrate a structure where the retractable hypodermic needle 26 of this invention is used in connection with a phlebotomy set 54. The phlebotomy set is configured for the direct withdrawal of blood from the patient to a blood collection tube 56. The needle holder 58 of the phlebotomy set is of similar configuration to the syringe barrel 12. It carries a nozzle 22 with a Luer lock thereon which is the same as the Luer lock 16 on syringe barrel 12. The difference is internal of the phlebotomy set and does not affect the operation of the needle assembly 26. The blood collection tube 56 has an elastomeric cap thereon and the blood collection tube has a vacuum therein. The blood collection tube may contain chemicals for preserving the blood or for other purposes with respect to the blood. Thus, the blood collection tube 56 is an independent structure. Interiorly of the needle holder 58 is a tubular needle directed toward the blood collection tube 56. The interior tubular needle is in line with and is connected to the nozzle 22 and its passage 24. The phlebotomy set is used by placing the needle assembly 26 on the needle holder 58. This extends the needle tip from the needle sheath 34 as shown in FIG. 7. The medical person then inserts the needle into the vein. When in position, the blood collection tube 56 is thrust down into the needle holder 58. Thereupon the puncture needle in the needle holder punctures the rubber cap on the blood collection tube 56. The vacuum in the blood collection tube withdraws blood from the patient, through the needle, through the sealed Luer connection, through the puncture tube into the blood collection tube. The hypodermic needle must be first inserted into the patient, before the advance of the blood collection tube so that the vacuum in the blood collection tube is not lost due to premature puncturing of its cap. After the collection is completed, the blood collection tube 56 is removed from the needle holder and the needle assembly 26 is removed from the needle holder. The removal of the needle assembly withdraws the needle 36 into its sheath 34. Thereupon, the needle assembly can be disposed. The blood collection tube goes to the laboratory and the needle holder can be sterilized for re-use, or disposed.

The needle assembly 26 can also be used with an intravenous drip tube, as shown in FIG. 8. The intravenous tube 60 comes from an IV fluid bag and through a dispensing pump. The end of the IV tube is provided with a Luer lock 62, the same as the Luer lock 16. When IV fluid is to be administered, the needle assembly 26 is attached to the Luer lock 62. This extends the needle 36 out of its sheath 34 so that the needle can be inserted into the patient's vein. The system remains in place until completion of the fluid transfer. Thereupon, the needle is withdrawn from the patient and the needle assembly is released from the Luer lock. The release from the Luer lock permits the spring to withdraw the needle into its sheath, therefore protecting personnel against inadvertent needle sticks. An effective protection of needles has been created.

This invention has been described in its presently contemplated best modes and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A retractable hypodermic needle assembly comprising:
a body, said body having a needle end and an attachment end, an attachment structure on the attachment end of said body for attachment to a device which handles biologically-active materials, said attachment structure comprising a Luer lock structure for engaging a Luer lock on a device for handling biological fluids and a cavity in said body for receiving the nozzle of said Luer lock;
a tubular needle sheath on the needle end of said body, a tubular hypodermic needle having a fluid passage therethrough, said hypodermic needle being slidably mounted in said needle sheath from a first position where said needle does not extend from said needle sheath to a second position wherein said needle extends from said needle sheath said body having no biologically active material space except in said needle passage;
a compression spring interengaged between said needle and said body to urge said needle towards said first position; and
a seal structure within said cavity in said body for sealing said needle with respect to a device for handling biologically active fluids.

2. The retractable hypodermic needle assembly of claim 1 wherein said cavity is a seal cavity in said body and there is a resilient seal member within said cavity, said resilient seal member being positioned to engage both said needle and said body.

3. The retractable hypodermic needle assembly of claim 1 wherein said assembly consists of a body carrying a needle sheath, a needle carrying a spring stop, a spring, and a seal.

4. The retractable hypodermic needle assembly of claim 2 wherein the nozzle of the Luer lock extends into said cavity and engages against said seal and forces said needle from said first position to said second position wherein said needle is exposed from said sheath.

5. The retractable hypodermic needle assembly of claim 4 wherein said resilient seal member is a ball engaging in said cavity, and said ball has a hole therethrough, said needle extending through said hole in said ball so that said ball seals said needle in said cavity.

6. The retractable hypodermic needle assembly of claim 4 wherein there is a stop on said hypodermic needle and said seal member engages against said stop so that said seal member and said stop forces said needle from its first position to its second position when said seal member is engaged by the nozzle on the Luer lock on the biologically-active material handling device.

7. The retractable hypodermic needle assembly of claim 6 wherein said stop is a collar on said needle and there is a spring engaged between said collar and said body to urge said needle toward its first position.

8. The retractable hypodermic needle assembly of claim 7 wherein said resilient seal member is a ball engaging in said cavity, and said ball has a hole therethrough, said needle extending through said hole in said ball so that said ball seals said needle in said cavity.

9. A retractable hypodermic needle assembly comprising:
a body, said body having an attachment end and a needle end, said attachment end of said body being configured to receive and attach to a Luer lock on a biologically-active fluid-handling device wherein the Luer lock has a nozzle thereon which extends into said body when said body is attached to a Luer lock;
a tubular needle sheath on said needle end of said body, a cavity in said body, a needle opening in said tubular needle sheath, said needle opening extending into said cavity in said body;
a hypodermic needle slidably mounted within said needle sheath, said hypodermic needle extending into said cavity, a spring structure interengaged between said needle and said body to urge said needle to a first position with respect to said body wherein said needle is retracted into said needle sheath, said needle and said sheath being configured so that when said needle is in a second position with respect to said body, said hypodermic needle extends out of said tubular needle sheath to a sufficient extent to be able to be used for hypodermic needle purposes; and
a seal within said body interengaged between said needle and said body to seal said needle to the nozzle of a Luer lock when said body is attached to a biologically-active fluid-handling device.

10. The retractable hypodermic needle assembly of claim 9 wherein there is a stop on said needle, said seal engaging said stop and sealing said needle within said cavity.

11. The retractable hypodermic needle assembly of claim 10 wherein said attachment end of said assembly is configured so that the nozzle of a Luer lock can extend into said cavity and is configured so that when a Luer lock is engaged therein, the nozzle of the Luer lock thrusts said needle from its first position to its second position so that whenever said assembly is attached to a Luer lock, said needle is in its second position and whenever said needle assembly is unattached to a Luer lock, said needle is in its first position.

12. The retractable hypodermic needle assembly of claim 9 wherein said seal is sized and positioned to be engaged by the nozzle of the Luer lock and said seal engages the needle to thrust said needle from its first to its second position.

13. The retractable hypodermic needle assembly of claim 9 wherein there is a stop collar on said needle and there is a spring in said body engaging said stop collar to thrust said needle toward its first position and said seal engages against said collar so that when the nozzle of the Luer lock engages against said seal it moves said needle to its second position.

14. The retractable hypodermic needle assembly of claim 13 wherein said seal is a substantially spherical elastomeric seal with a needle hole therethrough and said seal is positioned to surround said needle and engage against said stop.

15. The retractable hypodermic needle assembly of claim 9 wherein the biologically active fluid handling device is a syringe and the barrel of said syringe carries the Luer lock.

16. The retractable hypodermic needle assembly of claim 9 wherein the biologically active fluid handling device is a phlebotomy set and the needle holder of said phlebotomy set carries the Luer lock.

17. The retractable hypodermic needle assembly of claim 9 wherein the biologically active fluid handling device is an intravenous line which carries the Luer lock thereon.

18. The method of exchanging biologically active fluid between a biologically active fluid handling device and a patient comprising the steps of:
attaching a retractable hypodermic needle assembly onto a Luer lock of a biologically active fluid handling device wherein the hypodermic needle assembly has a cavity therein to receive the nozzle of the Luer lock and has a needle sheath which completely contains the hypodermic needle in a first position;
attaching the assembly to the Luer lock so that the nozzle of the Luer lock engages the needle and thrusts the needle to a second position where the needle extends from the sheath;
puncturing the patient with the hypodermic needle and exchanging biologically active fluid between the patient and the biologically active fluid handling device;
withdrawing the needle from the patient; and
removing the hypodermic needle assembly from the Luer lock so that an internal spring structure within the body withdraws the needle into the sheath into the first position so that the needle is fully engaged in the sheath in the protected position.

19. The retractable hypodermic needle assembly of claim 10 wherein there is a lip in said seal cavity, said lip holding said seal within said cavity to hold said hypodermic needle assembly in said first position retracted inside said sheath.

20. A retractable hypodermic needle assembly comprising:
a body, said body having a needle end and an attachment end, attachment structure on the attachment end of said body for direct attachment to a device which handles biologically-active materials;
a tubular needle sheath secured directly on the needle end of said body, a tubular hypodermic needle slidably mounted in said needle sheath from a first position where said needle does not extend from said needle sheath to a second position wherein said needle extends from said needle sheath;
a spring structure interengaged directly between said needle and said body to urge said needle towards said first position; and
a seal structure within said body directly engaging said body and said needle for sealing said needle with respect to a device for handling biologically active fluids.

* * * * *